(12) United States Patent
Elfsberg et al.

(10) Patent No.: US 7,825,291 B2
(45) Date of Patent: Nov. 2, 2010

(54) ABSORBENT ARTICLE HAVING ABSORBENT CORE INCLUDING REGIONS OF LOWER THICKNESS

(75) Inventors: Camilla Elfsberg, Torslanda (SE); Leif Wallström, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 63 days.

(21) Appl. No.: 11/965,898

(22) Filed: Dec. 28, 2007

(65) Prior Publication Data

US 2008/0103468 A1     May 1, 2008

Related U.S. Application Data

(63) Continuation of application No. PCT/SE2005/001150, filed on Jul. 13, 2005.

(51) Int. Cl.
    *A61F 13/15*      (2006.01)
    *A61F 13/20*      (2006.01)

(52) U.S. Cl. .................. 604/378; 604/385.01; 604/380; 604/379; 604/317; 604/358; 604/365; 604/367; 604/384; 604/382; 604/385.04; 604/385.03

(58) Field of Classification Search .................. 604/378, 604/385.01, 380, 379, 317, 358, 365, 367, 604/382, 384, 385.04, 385.03
See application file for complete search history.

(56) References Cited

U.S. PATENT DOCUMENTS 3,442,268 A *   5/1969   Bird ............................ 604/380

(Continued)

FOREIGN PATENT DOCUMENTS

EP    0 572 033 (A2)    12/1993

(Continued)

OTHER PUBLICATIONS

Form PCT/ISA/210 (International Search Report) dated Feb. 6, 2006.

(Continued)

*Primary Examiner*—Tatyana Zalukaeva
*Assistant Examiner*—Ginger T Chapman
(74) *Attorney, Agent, or Firm*—Buchanan Ingersoll & Rooney PC (57) ABSTRACT

An absorbent article 10 has front 12, crotch 14 and rear 16 portions. The article has an absorbent core 18 of unitary construction and of uniform density, which is defined by a pair of opposing longitudinal edges 20;22 and a pair of opposing transverse edges 24;26. The absorbent core 18 has at least a first 28 and a second 30 region, the average thickness of the absorbent core 18 in these first and second regions 28, 30 being lower than the average thickness of the absorbent core 18 surrounding the first and second regions 28;30, the first and second lower thickness regions 28;30 being arranged symmetrically about the longitudinal center line A of the article such that each of the first and second lower thickness regions 28;30 extends to the respective longitudinal edge 20;22 of the absorbent core. The distance $a_x$ between the first and second lower thickness regions 28;30 in the transverse direction varying along the longitudinal direction of the article. A minimum distance $a_1$ between the first and second lower thickness regions 28;30 in the transverse direction is located at least in the transition 32 between the crotch portion 14 and the front portion 12. The article provides good, secure fit and high comfort to the wearer.

28 Claims, 7 Drawing Sheets

U.S. PATENT DOCUMENTS

| | | | |
|---|---|---|---|
| 4,001,585 A * | 1/1977 | Coutarel | 250/328 |
| 4,027,672 A * | 6/1977 | Karami | 604/380 |
| 4,443,512 A * | 4/1984 | Delvaux | 428/162 |
| 4,758,240 A * | 7/1988 | Glassman | 604/379 |
| 4,765,780 A | 8/1988 | Angstadt | |
| 4,781,710 A * | 11/1988 | Megison et al. | 604/378 |
| 5,312,386 A * | 5/1994 | Correa et al. | 604/379 |
| 5,505,720 A * | 4/1996 | Walters et al. | 604/378 |
| 5,514,104 A * | 5/1996 | Cole et al. | 604/366 |
| 5,795,344 A * | 8/1998 | Chappell | 604/379 |
| 5,833,679 A * | 11/1998 | Wada | 604/384 |
| 5,941,863 A * | 8/1999 | Guidotti et al. | 604/378 |
| 6,056,732 A * | 5/2000 | Fujioka et al. | 604/385.01 |
| 6,160,197 A * | 12/2000 | Lassen et al. | 604/358 |
| 6,362,391 B1 * | 3/2002 | Mizutani et al. | 604/379 |
| 6,521,811 B1 * | 2/2003 | Lassen et al. | 604/378 |
| 6,563,013 B1 * | 5/2003 | Murota | 604/380 |
| 6,605,752 B2 * | 8/2003 | Magnusson et al. | 604/379 |
| 6,673,057 B1 | 1/2004 | Ehrnsperger et al. | |
| 6,766,817 B2 | 7/2004 | da Silva | |
| 6,918,404 B2 | 7/2005 | da Silva | |
| 7,066,586 B2 | 6/2006 | da Silva | |
| 7,285,255 B2 | 10/2007 | Kadlec | |
| 7,312,372 B2 * | 12/2007 | Miyama et al. | 604/380 |
| 7,388,123 B2 * | 6/2008 | Cowell et al. | 604/382 |
| 2003/0119401 A1 | 6/2003 | Chakravarty et al. | |
| 2004/0122407 A1 | 6/2004 | Hernandez et al. | |
| 2004/0204698 A1 * | 10/2004 | Zenker et al. | 604/367 |

FOREIGN PATENT DOCUMENTS

| | | |
|---|---|---|
| EP | 0 956 844 (A2) | 11/1999 |
| EP | 0 969 784 (B1) | 1/2000 |
| EP | 1 035 818 (B1) | 9/2000 |
| EP | 1 102 824 (B1) | 5/2001 |
| EP | 1 253 231 (B1) | 10/2002 |
| EP | 1 275 358 (A2) | 1/2003 |
| EP | 1 458 718 (B1) | 9/2004 |
| SE | 508 839 (C2) | 11/1998 |
| WO | WO 98/43571 (A1) | 10/1998 |
| WO | WO 99/51699 (A1) | 10/1999 |
| WO | WO 02/085269 (A1) | 10/2002 |
| WO | WO 02/085270 (A1) | 10/2002 |
| WO | WO 02/087483 (A1) | 11/2002 |
| WO | WO 02/087484 (A1) | 11/2002 |
| WO | WO 03/047484 (A1) | 6/2003 |
| WO | WO 03/051878 (A1) | 6/2003 |
| WO | WO 03/053301 (A1) | 7/2003 |
| WO | WO 03/059222 (A1) | 7/2003 |
| WOWO | 2006/059922 (A1) | 6/2006 |

OTHER PUBLICATIONS

Form PCT/ISA/237 (Written Opinion of the International Searching Authority) dated Feb. 6, 2006.

* cited by examiner

ABSORBENT ARTICLE HAVING ABSORBENT CORE INCLUDING REGIONS OF LOWER THICKNESS

CROSS-REFERENCE FOR RELATED APPLICATIONS

The present application is a continuation of PCT/SE2005/001150, filed on Jul. 13, 2005, the entire contents of which are incorporated herein.

FIELD OF THE INVENTION

The present invention relates to absorbent articles, such as sanitary towels, panty liners, incontinence pads or diapers which are designed so that they adopt a particular form when in use. Certain regions of the article which are thinner than other regions allow the article to take on a desired form and minimise the problems associated with the article moving out of place on the user's body.

BACKGROUND TO THE INVENTION

As well as good absorptive properties, primary requirements of absorbent articles are good fit and comfort. Various methods have been employed in the design and manufacture of absorbent articles so that they follow the contours of the user's body well and do not move out of place during use.

Patent applications WO 03/053301, EP 0 956 844, WO 03/047484, WO 02/087484, WO 02/085270, WO 03/059222, WO 02/087483, WO 02/085269 and related applications describe absorbent products which comprise a stiffening element that is intended to contribute to the three-dimensional shape of the products during their use.

EP 1 458 718 describes a disposable diaper having a region of low stiffness being a rectangular region along each side edge of the absorbent member. The low bending stiffness of this region allows the diaper to be bent upwards easily to join around the waist of the user.

EP 1 275 358 describes an absorbent article having a front absorbent region and a rear cushion region. The stiffness is higher in the front absorbent region, such that the shape of the raised region is maintained.

US 2004/0122407 discloses a sanitary napkin, the longitudinal central region of which has a higher flexure-resistance than the outer portions. In this way, the side regions are flexible enough that the sanitary napkin forms a cup-like trough under the wearers' genitals.

EP 0 572 033 discloses an absorbent article having zones which vary in stiffness. The article resists bunching and twisting during use. EP 1 102 824 discloses a sanitary napkin, the edges of which are less stiff than the center for comfort.

US2004/0204698 and US2003/0119401 describe an absorbent article having an air-formed unitary absorbent core. The core provides non-uniform lateral compression stiffness and predetermined bending in the article, as it has thinner regions at the edges. The core is thinner towards the front/rear edges as well as at the side edges.

There is still room for improvement in the comfort and fit of absorbent articles such as sanitary napkins. In particular, many of the earlier approaches to this problem involve cutting or otherwise removing parts of the absorbent cores of absorbent articles. However, this reduces the total amount of absorbent material which is present and thus provides lower security against leakage. Furthermore, cutting or otherwise removing parts of the absorbent core often results in wasted material, as the cut-out parts cannot always be used. Furthermore, many known products require additional stiffening elements.

OBJECTS AND SUMMARY

The present disclosure addresses the problems associated with the prior art in this area. Particularly, it provides an absorbent article which combines the features of softness and comfort with good fit and correct, secure placement of the article on the wearer. Cutting or otherwise removing parts of the absorbent core in the plane of the core may be avoided, providing more absorbent material (and thus higher absorption capacity) and giving the wearer the impression of a more "complete" article (thus improving wearer confidence). The effects are achieved solely through the absorbent core of the article, thus avoiding the use of additional stiffening elements. The articles can also be manufactured using existing equipment, with only minor modifications to current processes.

According to a first embodiment, an absorbent article, such as a sanitary towel, a panty liner, an incontinence pad or a diaper, has transverse and longitudinal directions. The article has front, crotch and rear portions. The article comprises an absorbent core of unitary construction and uniform density, said absorbent core being defined by a pair of opposing longitudinal edges and a pair of opposing transverse edges. The absorbent core has at least a first and a second region, the average thickness of the absorbent core in these first and second regions being lower than the average thickness of the absorbent core surrounding said first and second regions. The first and second lower thickness regions are arranged symmetrically about the longitudinal center line of the article. The first and second lower thickness regions extend to the respective longitudinal edges of the absorbent core, and the distance between said first and second lower thickness regions in the transverse direction varies along the longitudinal direction of the article. A minimum distance between said first and second lower thickness regions in the transverse direction is located at least in the transition between the crotch portion and the front portion of the article.

In a further embodiment, the article further comprises a third region having an average thickness which is lower than the average thickness of the absorbent core surrounding said third region, said third lower thickness region being located in the rear portion of the article. This third lower thickness region extends to the transverse edge of the absorbent core. The third lower thickness region has an axis of symmetry lying on the longitudinal center line of the article.

In a third embodiment, the absorbent article is symmetric about the transverse center line, and the distance between said first and second lower thickness regions in the transverse direction has a further minimum located in the transition between the crotch portion and the rear portion. The article further comprises a sixth lower thickness region having an average thickness which is lower than the average thickness of the absorbent core surrounding said sixth region. The sixth lower thickness region is located in the front portion of the article, and extends to the transverse edge of the absorbent core. The sixth lower thickness region has an axis of symmetry lying on the longitudinal center line of the article. Such an article may be placed either way round on the user.

In a fourth embodiment, the absorbent article is symmetric about the transverse center line and the absorbent core additionally has a fourth and a fifth region. The average thickness of the absorbent core in these fourth and fifth regions is lower than the average thickness of the absorbent core surrounding said fourth and fifth regions. The fourth and fifth lower thickness regions are arranged symmetrically about the longitudinal center line of the article, and extend to the respective longitudinal edges of the absorbent core. The distance between the fourth and fifth lower thickness regions in the transverse direction varies along the longitudinal direction of the article, and a minimum distance between said fourth and fifth lower thickness regions in the transverse direction is located at least in the transition between the crotch portion and the rear portion. The article further comprises a sixth region having an average thickness which is lower than the average thickness of the absorbent core surrounding said sixth region, said sixth lower thickness region being located in the front portion of the article and extending to the transverse edge of the absorbent core. The sixth lower thickness region has an axis of symmetry lying on the longitudinal center line of the article.

Preferably, the maximum extension of the first and second lower thickness regions in the longitudinal direction is less than the total extension of the absorbent article in the longitudinal direction. Suitably, the maximum extension of the first and second lower thickness regions bx in the longitudinal direction is between 3-10 cm, more preferably between 4-8 cm, most preferably between 5-7 cm.

Similarly, the maximum extension of the third lower thickness region in the transverse direction may be less than the total extension of the absorbent article in the transverse direction. The maximum extension of the third lower thickness region in the transverse direction is suitably less than 75%, more preferably less than 50%, most preferably less than 25% of the total extension of the absorbent article in the transverse direction.

In an absorbent article, the distance between the first and second lower thickness regions in the transverse direction of the article is preferably greater at the crotch point of the article than in the transition between the crotch portion and the front portion.

In one embodiment, the first, second, third and any further lower thickness regions have a lowest thickness which is at least 20% lower, more preferably at least 30% lower and most preferably at least 50% lower than the thickness of the absorbent core surrounding these regions. In another embodiment, the thickness of the first, second, third and any further lower thickness regions varies such that it increases gradually towards the edges of said regions, and reaches 100% of the thickness of the absorbent core surrounding these regions, at the edges of the regions where they meet the remainder of the absorbent core.

The minimum distance between said first and second lower thickness regions in the transverse direction, located in the transition between the crotch portion and the front portion is preferably between 15 and 45 mm, more preferably between 20 and 30 mm.

The absorbent article may further comprise lines or markings on the wearer-facing side of the absorbent core which indicate the location of the lower thickness areas.

In addition to the absorbent core, the absorbent article may further comprise an inner coversheet and an outer coversheet. Suitably, the absorbent core is not joined to the outer coversheet in any of the lower thickness regions. The minimum total thickness of the article is preferably at least 3 mm, more preferably at least 5 mm.

DETAILED DESCRIPTION OF THE PREFERRED EMBODIMENTS

An absorbent article 10 may be a sanitary towel, a panty liner, an incontinence pad or a diaper. Preferably, the absorbent article 10 is a sanitary towel. Such articles are commonly used for acquisition and storage of bodily exudates such as urine, faeces or menstrual fluid. The absorbent article is preferably disposable—i.e. it is intended to be used only once and disposed thereafter, rather than being cleaned and re-used.

Figure 1:
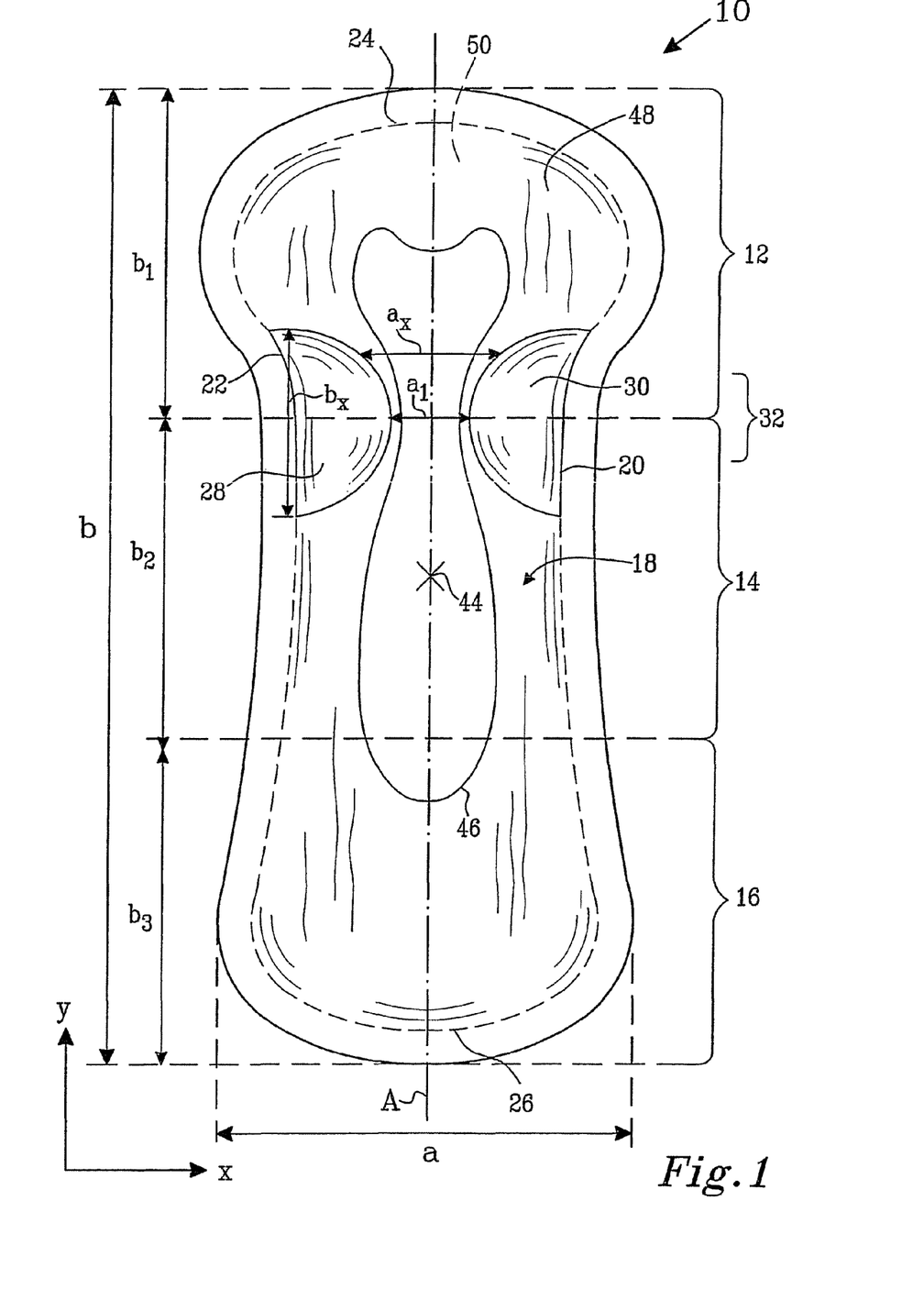
FIG. 1 shows an embodiment of the invention which is a sanitary towel.

FIG. 1 shows an embodiment of the present invention which is a sanitary towel. The article has transverse x and longitudinal y directions as indicated. The total length of the article in the transverse direction is length a, while the total length of the article in the longitudinal direction is length b.

The article further has front 12, crotch 14 and rear 16 portions arranged in the article's longitudinal direction. In use, the front portion 12 of the article is intended to cover the pubic region of the wearer. The front portion 12 is defined by the front transverse edge of the article and extends a certain length b1 along the article in the longitudinal direction. In a sanitary napkin of the type shown, the front portion 12 has a length b1 in the longitudinal direction which is between 10-50%, more preferably between 25-40%, most preferably between 30-35% of the total length b of the article.

The crotch portion 14 of the article is located adjacent to the front portion 12 in the longitudinal direction. In use, the crotch portion lies between the legs of the user and covers the user's genital region and perineum. In a sanitary napkin of the type shown, the crotch portion 14 has a length b2 in the longitudinal direction which is between 10-50%, more preferably between 25-40%, most preferably between 30-35% of the total length b of the article. Typically, the length b2 of the crotch portion 14 in the longitudinal direction is between 40-110 mm, more preferably between 50-105 mm, most preferably between 85-100 mm. The transition 32 between the front portion 12 and the crotch portion 14 is the border area between the front and crotch portions.

The rear portion 16 is located at the opposite end of the article from the front portion 12 and is located adjacent to the crotch portion 14 in the longitudinal direction. In use, the rear portion 16 extends towards the user's rear. The rear portion 16 is defined by the rear transverse edge of the article and extends a certain length b3 along the article in the longitudinal direction. In a sanitary napkin of the type shown, the rear portion 16 has a length b3 in the longitudinal direction which is between 10-50%, more preferably between 25-40%, most preferably between 30-35% of the total length b of the article.

In addition to the absorbent core 18 described herein, absorbent articles typically comprise an inner coversheet 48 and an outer coversheet 50. The inner coversheet 48 lies in direct contact with the wearer's body, and should therefore be soft, comfortable and liquid-permeable. The inner coversheet can comprise a nonwoven material, e.g. spunbond, meltblown, carded, hydroentangled, wetlaid etc. Suitable nonwoven materials can be composed of natural fibres, such as wood pulp or cotton fibres, manmade fibres, such as polyester, polyethylene, polypropylene, viscose etc. or from a mixture of natural and man-made fibres. The inner coversheet material may further be composed of tow fibres, which may be bonded to each other in a bonding pattern, as e.g. disclosed in EP-A-1 035 818. Further examples of inner coversheet materials are porous foams, apertured plastic films etc. The materials suited as inner coversheet materials should be soft and non-irritating to the skin and be readily penetrated by body fluid, e.g. urine or menstrual fluid. The inner coversheet may further be different in different parts of the absorbent article.

The outer coversheet 50 lies in contact with the wearer's garments, and is liquid-impermeable. The outer coversheet refers to the liquid impervious material forming the outer cover of the absorbent article. The outer coversheet can comprise a thin plastic film, e.g. a polyethylene or polypropylene film, a nonwoven material coated with a liquid impervious material, a hydrophobic nonwoven material, which resists liquid penetration, or a laminate of a plastic film and a nonwoven material. Other laminate materials which are suitable for use as the outer coversheet are laminates of a nonwoven material and high-loft wadding material. The outer coversheet material may be breathable so as to allow vapour to escape from the absorbent core, while still preventing liquids from passing therethrough.

Examples of breathable outer coversheet materials are porous polymeric films, nonwoven laminates of spunbond and meltblown layers and laminates of porous polymeric films and nonwoven materials. Preferably, the outer coversheet comprises nonwoven material in at least the garment-facing surface thereof.

In an alternative embodiment, the absorbent article 10 may only comprise an outer coversheet. Additionally, the absorbent core 18 of the absorbent article may be wrapped in a single coversheet which can act as both inner and outer coversheet.

In one embodiment, the absorbent core 18 is not joined to the outer coversheet 50 in any of the lower thickness regions. This allows the absorbent core 18 and the inner and outer coversheets of the article to deform independently of each other. The inner and outer coversheets do not therefore hinder the deformation of the absorbent core. The article follows the contours of the user's body more closely and provides the article with greater flexibility.

The absorbent article may further include an acquisition distribution layer (not shown) which is placed on top of the absorbent core and adapted to quickly receive and temporarily store discharged liquid before it is absorbed by the absorbent core. Such acquisition distribution layers are well known in the art and may be composed of porous fibrous wadding, SD plastic film, LDA (low density airlaid), multibond, latex bonded or foam materials.

The absorbent article 10 comprises an absorbent core 18 of unitary construction. The "absorbent core" is the absorbent structure of the article which acquires and stores bodily fluids. The absorbent core can be of any conventional kind. Examples of commonly occurring absorbent materials are cellulosic fluff pulp, tissue, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times their own weight of an aqueous solution containing 0.9 weight percent of sodium chloride. Organic materials suitable for use as a superabsorbent material can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water insoluble. Preferred superabsorbent materials are further surface cross-linked so that the outer surface or shell of the superabsorbent particle, fibre, flake, sphere, etc. possesses a higher crosslink density than the inner portion of the superabsorbent. The superabsorbent materials may be in any form suitable for use in absorbent composites including particles, fibres, flakes, spheres, and the like. A high absorption capacity is provided by the use of high amounts of superabsorbent material.

The thin absorbent bodies, which are common in for example baby diapers and incontinence guards, often comprise a compressed, mixed or layered structure of cellulosic fluff pulp and superabsorbent polymers. The size and absorbent capacity of the absorbent core may be varied to suit different uses, such as infants or adult incontinent persons.

The phrase "unitary construction" in the present context is intended to mean that the absorbent core 18 is constructed from essentially one type of material, this being essentially the same material, or essentially the same combination of two or more materials throughout the absorbent core. Variations in concentration of the material may occur, but these are limited to those which can be obtained without incorporation of regions which have been formed separately and then physically joined to each other. For example, when the absorbent core comprises a matrix of hydrophilic fibres and superabsorbent material as described above, the relative concentrations of superabsorbent material and fibres may be different in different parts of the core. However, the absorbent core should not, for instance, comprise layers or laminates of different composition. Likewise, variations in the density or concentration of various components across the longitudinal or transverse directions of the absorbent core are acceptable, yet the core should not comprise areas or layers of different composition which are formed separately and later joined together.

Figure 5A:
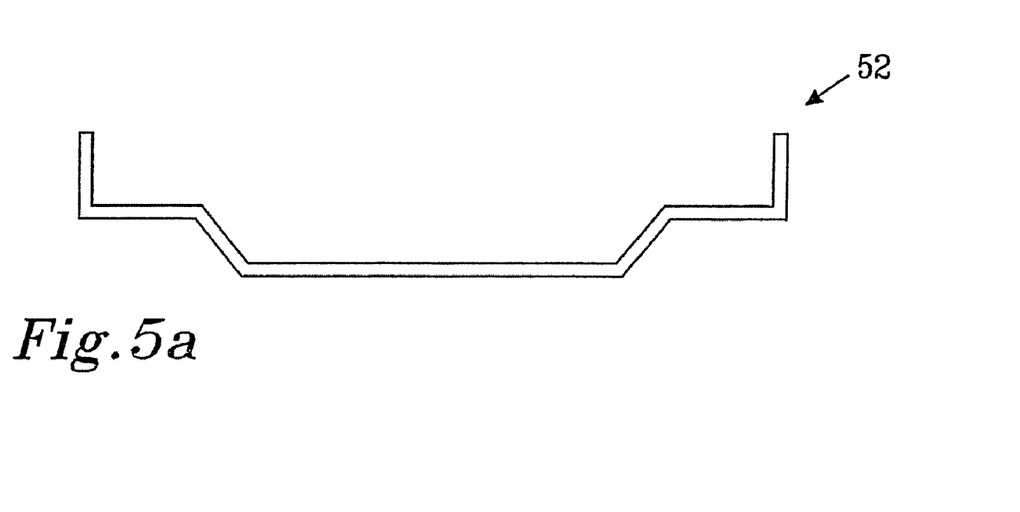
FIGS. 5, 6 and 7 are cross-sectional views of methods by which absorbent cores of the present invention may be produced.
Figure 5B:
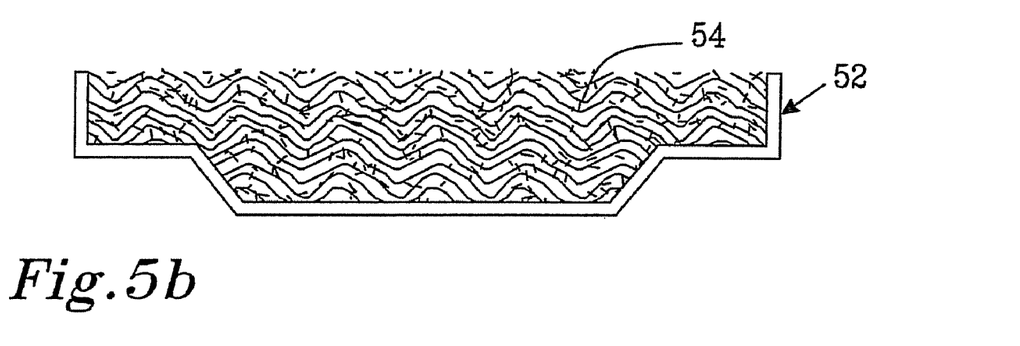
Figure 5C:
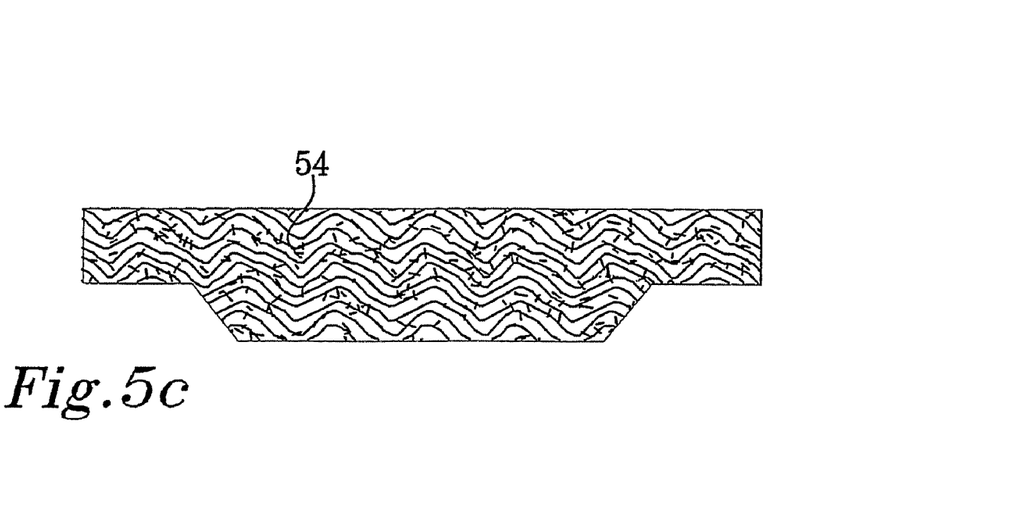

A suitable technique for forming the absorbent cores is mat-forming through an air-laying process, as illustrated in FIGS. 5*a-c* and as described more closely in EP-A2-1 253 231. An air-permeable mould 52 having the desired shape is provided. The depth of the mould varies, as seen in the cross-sectional view in FIG. 5*a*, according to the amount of material which is required at each point. Fibrous material 54 is air-laid into the mould, and the mould is filled such that uniform density is obtained in the core (see FIG. 5*b*). Due to the differences in the mould depth in various areas, the amount of fibrous material at each point will vary (FIG. 5*c*). After the absorbent core is produced, it may be compressed so that a desired thickness of the core is obtained in various areas. Compressing may take place after the core has been removed from the mould, or alternatively while it is still in place. In this way, areas of different thickness can be built up within the absorbent core. If desired, masks or baffles may be introduced in the mat-forming process, so that fibre-laying in the unmasked areas is higher than in the masked areas. This allows further control over the material thickness.

In the efficient mat-forming processes of today, mat-forming wheels are used, as described in U.S. Pat. No. 4,765,780, SE 9401542-7 and EP-A2-1 253 231. The air-permeable moulds are evenly spaced about the periphery of the mat-forming wheels. Fibrous material (together with any other material which might be desired) is fed from mills by means of blowers and onto mat-forming wheels via mat-forming covers. More than one mat-forming cover may be present performing wheel.

In an alternative to forming in mat-forming wheels, the absorbent cores may be produced by laying fibrous material (together with any other material which might be desired) onto a web having a profile which ultimately gives a thickness difference on different parts of the material web. The material can be prefabricated and rolled up into rolls.

Figure 6A:
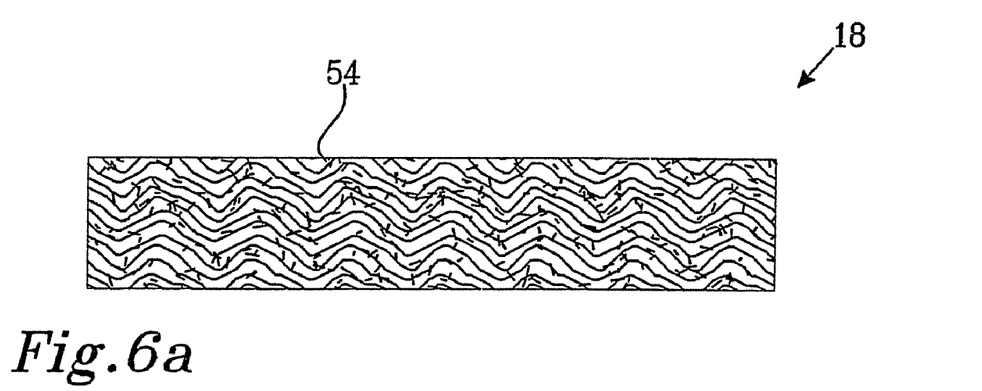
Figure 6B:
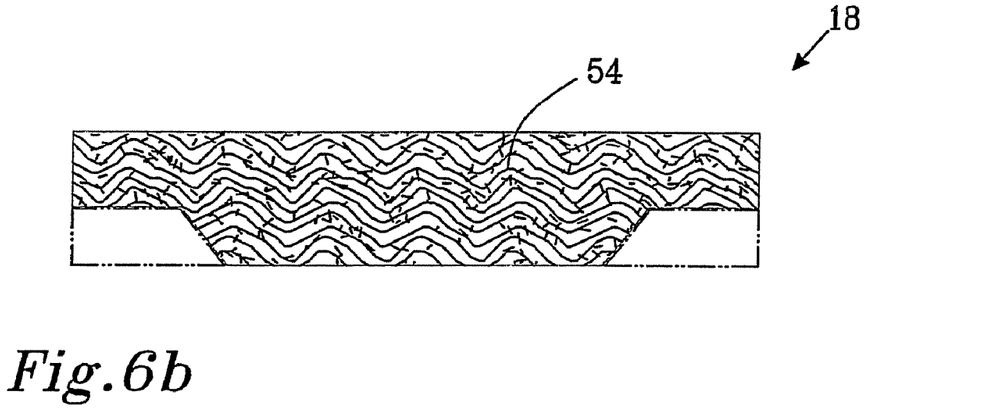

Absorbent cores 18 may also be produced according to the sequence shown in FIGS. 6*a-b*. A material having uniform density and the same thickness across the material is provided (FIG. 6*a*). It is preferred that this material has an internal strength such that it does not easily crumble or break when material is removed. A foam material is an example of a suitable material. A compact wadding material may also be considered. In this case, the material comprises binding fibres which can be melted together in a finely-porous wadding structure. Thin airlaid material with a lot of binding fibres may also be used.

In the next step (FIG. 6*b*), material is cut or milled out of the core 18 to provide thinner regions in the desired areas.

Figure 7A:
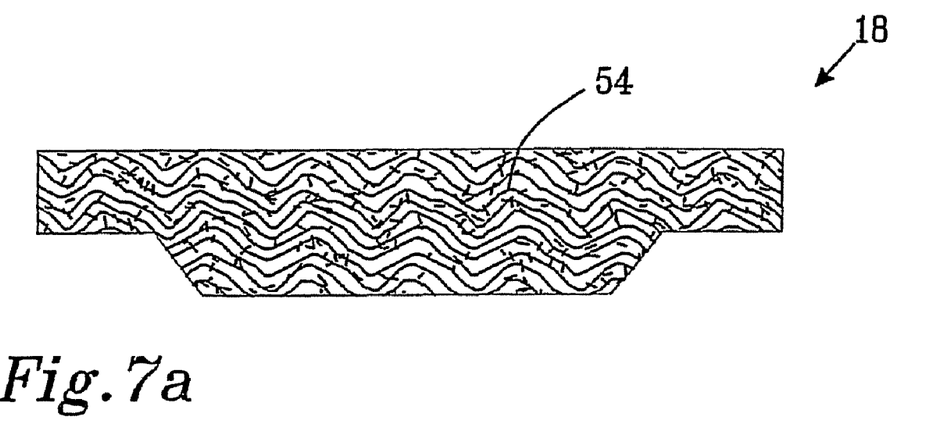
Figure 7B:
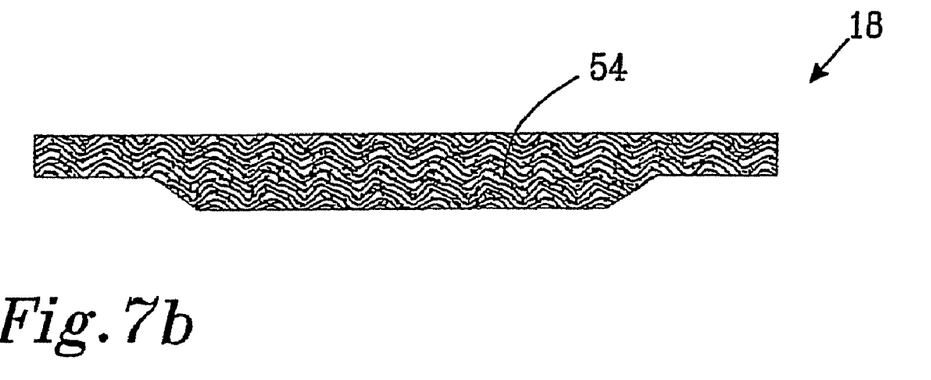

Absorbent cores 18 may also be produced according to the sequence shown in FIGS. 7*a-b*. An absorbent core 18 is provided, having uniform density, yet varying thickness in the desired regions. This may be obtained through any of the methods described above. The core is then compressed with a profiled press roll having contours which correspond to the desired regions. Compression should be the same across the entire core (the core may remain in its mould while compression takes place) so that the density over the entire core is the same, and the profile of the core is maintained. To obtain such a uniform compression, compression may take place while the core is still in the mould.

The absorbent core 18 according to the invention is of uniform density. By this is meant that the density of the absorbent core is not significantly different in any direction (longitudinal, transverse or through the thickness of the article).

The absorbent core 18 is defined by a pair of opposing longitudinal edges 20;22 and a pair of opposing transverse edges 24;26. The absorbent core does not necessarily have a parallelogram shape, but may have e.g. rounded edges or a dog-bone shape. In this case, the transition between transverse and longitudinal edges is defined as the point on the edge of the article at which the rate of curvature of the transverse edge of the article with respect to the transverse direction is greatest. In a preferred embodiment, the longitudinal edges of the article are substantially parallel.

The absorbent core 18 is thinner in at least a first 28 and a second region 30. That is, the first and second regions 28, 30 have an average thickness which is lower than the average thickness of the absorbent core surrounding these regions.

The first and second lower thickness regions 28;30 are arranged symmetrically about the longitudinal center line A of the article. This is so that the article lies symmetrically on the user's body when in use. By "arranged symmetrically" is meant each point in the first lower thickness region 28 has a corresponding point in the second lower thickness region 30; the two points being related to each other by reflection in a plane located on the longitudinal center line A of the article. The first and second lower thickness regions 28;30 are therefore mirror images of each other and are located in corresponding locations on opposite sides of the longitudinal center line A.

The first and second lower thickness regions 28;30 extend to the respective longitudinal edges 20;22 of the absorbent core. The distance $a_x$ between the first and second lower thickness regions 28;30 in the transverse direction of the absorbent article varies along the longitudinal direction of the article. That is, the edge of the first or second lower thickness regions 28;30 lying closest to the longitudinal center line A of the article is not parallel with this longitudinal center line A. The distance $a_x$ therefore exhibits maxima and minima along the longitudinal direction of the article. Preferably, the distance $a_x$ varies continuously along the longitudinal direction of the article.

A minimum distance $a_1$ between said first and second lower thickness regions 28;30 in the transverse direction is located at least in the transition 32 between the crotch portion 14 and the front portion 12. The distance between the lower thickness regions 28;30 may exhibit more than one minima, but preferably, there is one minimum distance a1, which lies in the transition 32.

The area around the crotch in which an absorbent article lies is defined in particular by two muscle tendons which are located down either side of the groin. These muscle tendons form part of the muscle group which originates on the inside of the pelvic diaphragm and has its attachment along the thigh. The muscle group consists of the adductor brevis, adductor longus, gracilis and adductor magnus muscles. In use, therefore, the absorbent article is placed between these muscle tendons, and the first and second lower thickness regions 28;30 are located between said tendons and compressed by them. Thus the term "transition between the crotch portion and the front portion" is herein defined as the region which in the intended use of the article is located between these two muscle tendons.

In that a minimum distance $a_1$ between said first and second lower thickness regions 28;30 in the transverse direction is located at least in the transition 32 between the crotch portion 14 and the front portion 12, the transition 32 is held correctly between these two tendons. The front portion 12 of the article is therefore held in the area in front of these tendons, while the crotch portion 14 of the article is positioned correctly against the genitals of the wearer. This helps to avoid problems associated with incorrect placement of the absorbent article, or movement of the article during wear. In particular, leg movements of the wearer often cause conventional sanitary towels to move backwards, which may be reduced by the present invention.

The distance between the two muscle tendons in the crotch of the wearer, which has been shown to be relatively constant for all people is around 25-45 mm. In around 80% of women, the distance between these two tendons is approximately 30-32 mm. The minimum distance $a_1$ between said first and second lower thickness regions 28;30 in the transverse direction is therefore preferably between 15 and 45 mm, more preferably between 20 and 30 mm. If the distance $a_1$ exceeds about 35 mm, the article is likely to feel uncomfortable for the majority of wearers. If the distance $a_1$ exceeds 45 mm, discomfort and chafing is highly likely to occur. Note that it is preferable that the minimum distance $a_1$ between said first and second lower thickness regions 28;30 in the transverse direction should be greater than zero; i.e. the first and second lower thickness regions should not overlap in the transverse direction.

Compression of the first and second lower thickness regions 28;30 of the absorbent article 10 in the transverse direction between the tendons in the inner thigh of the wearer also promotes formation of the correct 3-dimensional form of the article. In particular, transverse compression of the longitudinal edges 20;22 at the lower thickness portions allows the front portion 12 of the article to fold upwards towards the user, and a "bowl" shape can be formed. This allows closer, more secure fit of the article. Predetermined shaping of the absorbent article also reduces the risk of the article folding in an undesired manner, for example creating channels which may cause leakage.

After production, absorbent articles of the kind described herein are usually folded and packaged. Further advantages of the absorbent article are evident upon folding and packaging. As the article is substantially planar when not in use, folding and packaging of the absorbent article are simplified as compared to a three-dimensional article. Additionally, any creases or folds which are introduced when the article is packaged can remain present after the article has been removed from the packaging. This presents problems when the article is to be worn, as these residual creases or folds from the packaging process may cause the article to fold in an undesirable manner when in use, and may also form channels in the article along which liquid can easily run, increasing the likelihood of leakage. Introducing the lower thickness regions reduces the tendency of the article to retain creases or folds from the packaging process after being removed from the packaging and, as these lower thickness regions lie at the edges of the absorbent core of the article, the transport gradient tends to promote liquid flow away from the edges. In effect, any folds which exist in the article after the packaging has been opened are limited by the lower thickness areas.

A further effect of the areas of lower thickness is that they have larger pores and capillaries and therefore lower capillary action than the surrounding areas. A capillary gradient is therefore present in the article, so that liquid is absorbed more preferentially into the thicker (non-soft) areas. This leads to an article having improved security against leakage, as liquid will not be distributed into the lower thickness areas as much as the thicker areas.

Figure 2:
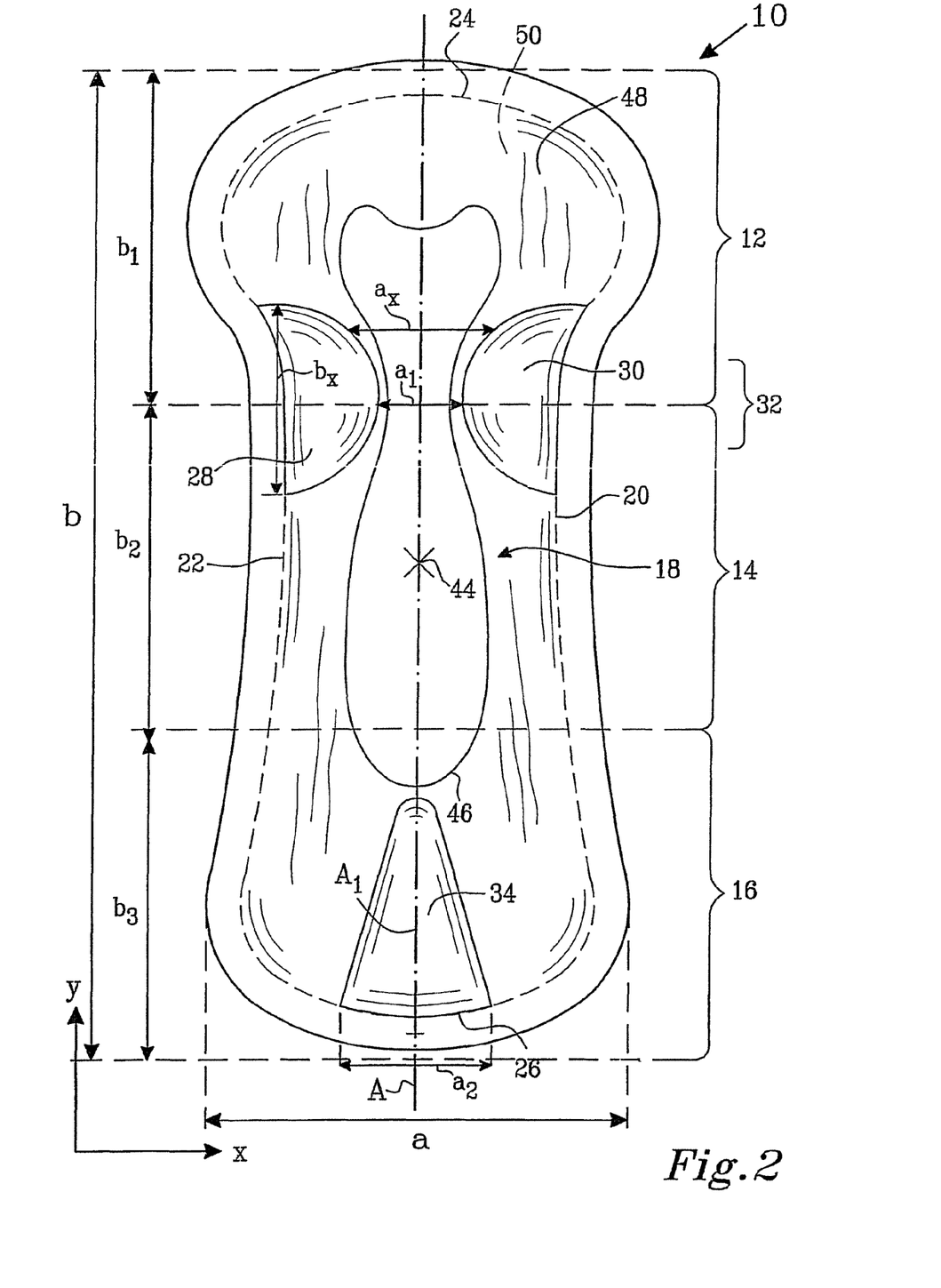
FIG. 2 shows an alternative arrangement of the lower thickness regions in an absorbent article.

In the embodiment shown in FIG. 2, the article further comprises a third region 34 having an average thickness which is lower than the average thickness of the absorbent core 18 surrounding said third region 34. This lower thickness third region 34 is located in the rear portion 16 of the article and extends to the transverse edge 26 of the absorbent core. As above, the absorbent core has uniform density. Again, to maintain symmetry of the article, the third lower thickness region 34 should have an axis of symmetry A1 which lies on the longitudinal center line A of the article. The third lower thickness region 34 may take any shape, as long as it is symmetrical about the longitudinal center line A of the article. A triangular shape as shown in FIG. 2 is particularly suitable for the third lower thickness region 34.

By means of this embodiment, the comfort and fit of the absorbent article are further increased. The absorbent article folds along the longitudinal center line A in the rear portion, and is thus accommodated in the cleft between the user's buttocks. This reduces the risk of leakage from the rear of the article. Furthermore, the third lower thickness region 34 introduces an absorption gradient in the rear portion of the article which deters liquid flow through this rear portion. Promoting a certain fold line in the rear portion increases the comfort of absorbent articles, as undesired twisting, bunching or Z-folding of the article between the buttocks is reduced. Folding of the rear portion 16 between the user's buttocks also promotes secure fit, as transverse and longitudinal movement of the article during wear is reduced. The third lower thickness region 34 in the rear portion 16 cooperates with the first and second lower thickness regions 28;30 to provide the article with a form which follows the contours of the wearer's body even more closely.

Figure 3:
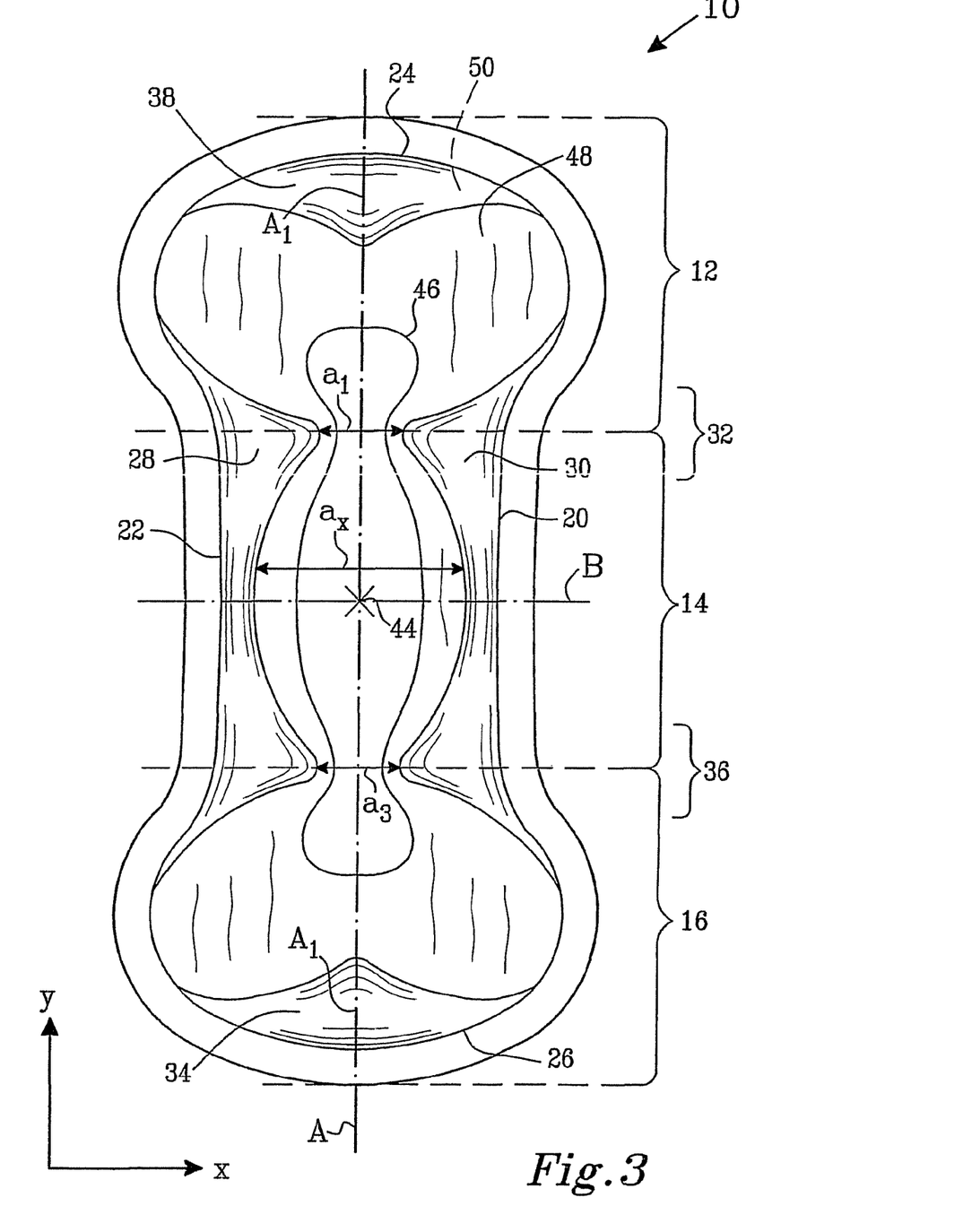
FIG. 3 shows another arrangement of the lower thickness regions in an absorbent article.

In the embodiment shown in FIG. 3, the article is symmetrical about the transverse center line B (i.e. the front and rear portions 12;16 are the same size and shape, and have the same length in the longitudinal direction). The article can therefore be placed upon the wearer in either direction. For this to occur, the distance $a_x$ between the first and second lower thickness regions 28;30 in the transverse direction exhibits a further minimum value a3 which is located in the transition 32 between the crotch portion 14 and the rear portion 16. The article further comprises a sixth region 38 having an average thickness which is lower than the average thickness of the absorbent core 18 surrounding said sixth region 38. The sixth lower thickness region 38 is located in the front portion 12 of the article, and extends to the transverse edge 24 of the absorbent core. As above, the absorbent core has uniform density. As with the third lower thickness region 34, said sixth lower thickness region 38 must also have an axis of symmetry A1 lying on the longitudinal center line A of the article. The article can thus be worn in either direction with the same good results.

Figure 4:
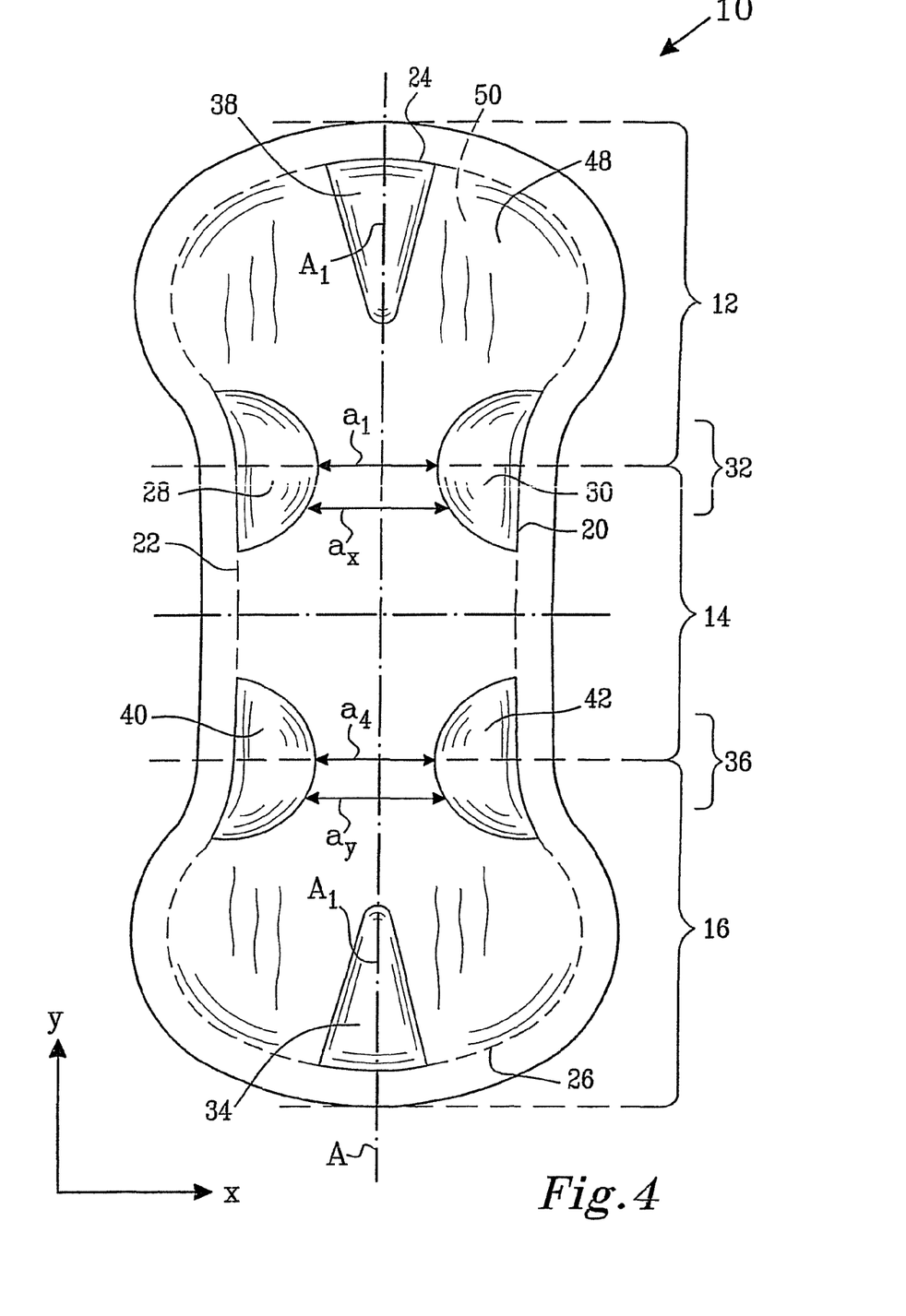
FIG. 4 shows another arrangement of the lower thickness regions in an absorbent article.

FIG. 4 shows an alternative way of obtaining an article which can be placed either way a round on the user. Instead of the first and second lower thickness regions 28;30 extending into the transition 32 between the crotch portion 14 and the rear portion 16, the article additionally has a fourth 40 and a fifth 42 region, the average thickness of the absorbent core 18 in these fourth and fifth regions 40, 42 being lower than the average thickness of the absorbent core 18 surrounding said fourth and fifth regions 40;42. These fourth and fifth lower thickness regions 40;42 are arranged symmetrically about the longitudinal center line A of the article and extend to the respective longitudinal edges 20;22 of the absorbent core 18. As above, the absorbent core has uniform density. In a similar way to above, the distance ay between the fourth and fifth lower thickness regions 40;42 in the transverse direction varies along the longitudinal direction of the article. A minimum distance a4 between said fourth and fifth lower thickness regions 40;42 in the transverse direction is located at least in the transition 32 between the crotch portion 14 and the rear portion 16. As above, the article further comprises a sixth region 38 having an average thickness which is lower than the average thickness of the absorbent core 18 surrounding said sixth region 38. This sixth lower thickness region 38 is located in the front portion 12 of the article, and extends to the transverse edge 24 of the absorbent core. As above, the absorbent core has uniform density. This sixth lower thickness region 38 has an axis of symmetry A1 lying on the longitudinal center line A of the article. The article according to this embodiment can be worn in either direction with the same good results.

The first and second lower thickness regions 28;30 have an extension along the article in the longitudinal direction. Increasing the longitudinal extension of these lower thickness regions provides the article with soft edges, which further increases comfort. However, the minimum distance $a_1$ between the first and second lower thickness regions 28;30 in the transverse direction should be at least in the transition 32 between the crotch portion 14 and the front portion 12. Preferably, the first and second lower thickness regions 28;30 do not extend along the entire length of the article in the longitudinal direction; i.e. the maximum extension $b_x$ of the first and second lower thickness regions 28;30 in the longitudinal direction y is less than the total extension b of the absorbent article in the longitudinal direction y. Suitably, the maximum extension $b_x$ of the first and second lower thickness regions 28;30 in the longitudinal direction y is between 3-10 cm, more preferably between 4-8 cm, most preferably between 5-7 cm.

In a similar manner, the maximum extension $a_2$ of the third lower thickness region 34 in the transverse direction x should be less than the total extension a of the absorbent article in the transverse direction x. The maximum extension $a_2$ of the third lower thickness region 34 in the transverse direction x is less than 75%, more preferably less than 50%, most preferably less than 25% of the total extension a of the absorbent article in the transverse direction x.

The absorbent core 18 of the article preferably does not have lower thickness at the "crotch point" of the article, as such lower thickness usually results in (undesirable) lower absorption properties. In this case, distance $a_x$ between said first and second lower thickness regions 28;30 in the transverse direction of the article is higher in the crotch point 44 of the article than in the transition 32 between the crotch portion 14 and the front portion 12. The "crotch point" is as defined in EP-B1-0 969 784 and described further in international application PCT/SE2004/001759. It is determined by placing the article on the wearer in a standing position, and then placing an extensible filament around the legs of the wearer in a figure-of-eight configuration. The point on the article corresponding to the point of intersection of the filament is deemed to be the crotch point 44. It should be understood that the crotch point is determined by placing the absorbent article on the wearer in the intended manner and determining where the crossing point of the filament would cross the article/core.

Preferably, the first 28, second 30, third 34 and any further lower thickness regions have a lowest thickness which is at least 20% lower, more preferably at least 30% lower and most preferably at least 50% lower than the thickness of the absorbent core surrounding these regions.

The thickness of the absorbent core surrounding the lower thickness regions is typically 3.5-12 mm, preferably 4.5-10 mm The density of the absorbent core is typically between 40-200 kg/m$^3$, preferably between 50-200 kg/m$^3$, more preferably between 70-90 kg/m$^3$. This allows the desired effects to be obtained while maintaining the absorption capacity.

The lower thickness regions may have a variable thickness which increases gradually towards the edges of said regions, such that it reaches 100% at the edges of the regions where they meet the remainder of the absorbent core. In this way, the resistance to stress of the first and second regions 28;30 increases as they are compressed. This allows a wider range of fit, as users with a narrower crotch will be able to compress the lower thickness regions more, while those with wider crotches will compress the lower thickness regions less. The articles will therefore fit the minority of people who do not have the above-mentioned ranges of the distance between the two muscle tendons. Additionally, the thickness gradient in these regions results in an absorption gradient, as thinner material has a lower capillary action. This provides additional security against leakage, as the absorption properties of the article decreases in the thinner regions towards the edges and fluid is directed towards the center of the article.

The various lower thickness regions 28, 30, 34, 38, 40, 42 may all have the same thickness. Alternatively, higher comfort may be provided by an absorbent article in which the lower thickness regions extending to the transverse edges—i.e. the third lower thickness region 34 and the sixth lower thickness region 38—have a lower thickness than the other regions. In use, the third or sixth lower thickness regions 34, 38 are located between the buttocks of the user, so that increased softness in these regions is desirable.

Material should be present in the lower thickness regions—the situation in which the thickness of the lower thickness areas is zero is not comprised within the scope of this invention.

A number of methods for measuring the thickness of absorbent cores, or the average thickness of samples, have been described in the literature. In particular, the average thickness of a sample of absorbent core may be measured according to the following procedure:

The absorbent article is carefully delaminated: any inner or outer coversheets are removed so as to only leave a unitary core.

A pressure of 0.5 kPa is applied to the absorbent core via a foot which corresponds in area to the area of the sample of absorbent core, the thickness of which is to be measured The thickness of the sample is measured while subject to this pressure.

The absorbent core 18 has a unitary appearance. This provides the wearer with a greater sense of security. However, the absorbent article 10 may further comprise lines or markings 46 on the wearer-facing side of the absorbent core 18. In this way, correct placement of the article is promoted and the location of the lower thickness areas is indicated. The lines or markings 46 can be compressed lines which form folding lines on the article and promote correct folding of the article when worn.

A sanitary towel may comprise any attachment means known in the art to allow fastening to undergarments of a wearer. Such means may include a coating of adhesive or friction coating on the garment-facing surface of the article, or attachment flaps ("wings") which extend in the transverse direction of the article and fold over the crotch portion of a user's undergarment. It is however important that the nature and placement of such attachment means does not significantly interfere with the function of the article in use.

The present invention is particularly relevant to relatively thick absorbent articles, such as relatively thick sanitary towels, in that they are bulky from the beginning and can give a close fit to the body. Such "thick" articles have a thickness lying between around 3 mm to around 12.5 mm, preferably 5-11 mm. However, they do not always fold in the required manner. The lower thickness regions of the present invention allow folding of the article to be directed, without bulky, uncomfortable edges being formed. The minimum thickness of a "thick" article according to the invention should be at least 3 mm, preferably at least 5 mm.

Although the above discussion has been exemplified through a sanitary napkin, the present invention is also applicable to other absorbent articles such as diapers, incontinence pads or panty-liners. For instance, application of the invention to diapers would provide similar benefits in terms of comfort, fit and leakage-prevention.

The invention should not be considered as limited by the above description; rather the scope and limitations of the invention are defined by the enclosed claims, and equivalents thereof.

The invention claimed is:

1. An absorbent article comprising transverse and longitudinal directions, said article further having front, crotch and rear portions arranged sequentially in the longitudinal direction, said article comprising an absorbent core of unitary construction and uniform density, said absorbent core being defined by a pair of opposing longitudinal edges extending substantially in the longitudinal direction and a pair of opposing transverse edges extending substantially in the transverse direction, said absorbent core having at least a first region and a second region, the average thickness of the absorbent core in these first and second regions being lower than the average thickness of the absorbent core extending around said first and second regions, the absorbent core extending around each of the first and second thinner regions from one point above the first or second thinner region in the longitudinal direction at a longitudinal edge of the absorbent core to a second point below the first or second region in the longitudinal direction at the same longitudinal edge of the absorbent core, said first and second thinner regions being arranged symmetrically with respect to each other about the longitudinal center line of the article and extending to the respective longitudinal edges of the absorbent core, the distance between said first and second thinner regions in the transverse direction varying along the longitudinal direction of the article, and a minimum distance between said first and second thinner regions in the transverse direction is located at least in the transition between the crotch portion and the front portion of the article.

2. The absorbent article according to claim 1, further comprising a third region having an average thickness which is lower than the average thickness of the absorbent core surrounding said third region, said lower thickness third region being located in the rear portion of the article, and extending to the rear transverse edge of the absorbent core, said third lower thickness region having an axis of symmetry lying on the longitudinal center line of the article.

3. The absorbent article according to claim 2, wherein the absorbent article is symmetric about the transverse center line, and the distance between said first and second lower thickness regions in the transverse direction has a further minimum located in the transition between the crotch portion and the rear portion and said article further comprises a sixth region having an average thickness which is lower than the average thickness of the absorbent core surrounding said sixth region, said sixth lower thickness region being located in the front portion of the article, and extending to the front transverse edge of the absorbent core, said sixth lower thickness region having an axis of symmetry lying on the longitudinal center line of the article.

4. The absorbent article according to claim 1, wherein the absorbent article is symmetric about the transverse center line and said absorbent core having a fourth and a fifth region, the average thickness of the absorbent core in these fourth and fifth regions being lower than the average thickness of the absorbent core surrounding said fourth and fifth regions, said fourth and fifth lower thickness regions being arranged symmetrically about the longitudinal center line of the article and extending to the respective longitudinal edges of the absorbent core, the distance between said fourth and fifth lower thickness regions in the transverse direction varying along the longitudinal direction of the article, and that a minimum distance between said fourth and fifth lower thickness regions in the transverse direction is located at least in the transition between the crotch portion and the rear portion and said article further comprises a sixth region having an average thickness which is lower than the average thickness of the absorbent core surrounding said sixth region, said sixth lower thickness region being located in the front portion of the article, and extending to the transverse edge of the absorbent core, said sixth lower thickness region having an axis of symmetry lying on the longitudinal center line of the article.

5. The absorbent article according to claim 1, wherein the maximum extension of the first and second lower thickness regions in the longitudinal direction is less than the total extension of the absorbent article in the longitudinal direction.

6. The absorbent article according to claim 4, wherein the maximum extension of the first and second lower thickness regions in the longitudinal direction is between 3-10 cm.

7. The absorbent article according to claim 4, wherein the maximum extension of the first and second lower thickness regions in the longitudinal direction is between 4-8 cm.

8. The absorbent article according to claim 4, wherein the maximum extension of the first and second lower thickness regions in the longitudinal direction is between 5-7 cm.

9. The absorbent article according to claim 2, wherein the maximum extension of the third lower thickness region in the transverse direction is less than the total extension of the absorbent article in the transverse direction.

10. The absorbent article according to claim 2, wherein the maximum extension of the third lower thickness region in the transverse direction is less than 75% of the total extension of the absorbent article in the transverse direction.

11. The absorbent article according to claim 2, wherein the maximum extension of the third lower thickness region in the transverse direction is less than 50% of the total extension of the absorbent article in the transverse direction.

12. The absorbent article according to claim 2, wherein the maximum extension of the third lower thickness region in the transverse direction is less than 25% of the total extension of the absorbent article in the transverse direction.

13. The absorbent article according to claim 1, wherein the distance between said first and second lower thickness regions in the transverse direction of the article is greater at the crotch point of the article than in the transition between the crotch portion and the front portion.

14. The absorbent article according to claim 2, wherein, the first, second, third and any further lower thickness regions have a lowest thickness which is at least 20% lower than the thickness of the absorbent core surrounding these regions.

15. The absorbent article according to claim 2, wherein, the first, second, third and any further lower thickness regions have a lowest thickness which is at least 30% lower than the thickness of the absorbent core surrounding these regions.

16. The absorbent article according to claim 2, wherein, the first, second, third and any further lower thickness regions have a lowest thickness which is at least 50% lower than the thickness of the absorbent core surrounding these regions.

17. The absorbent article according to claim 1, wherein the thickness of the first, second, third and any further lower thickness regions varies such that the thickness increases gradually towards the edges of said regions, and reaches 100% of the thickness of the absorbent core surrounding these regions at the edges of the regions where they meet the remainder of the absorbent core.

18. The absorbent article according to claim 1, wherein the minimum distance between said first and second lower thickness regions in the transverse direction, located in the transition between the crotch portion and the front portion is between 15 and 45 mm.

19. The absorbent article according to claim 1, wherein the minimum distance between said first and second lower thickness regions in the transverse direction, located in the transition between the crotch portion and the front portion is between 20 and 30 mm.

20. The absorbent article according to claim 1, wherein the absorbent article further comprises lines or markings on the wearer-facing side of the absorbent core.

21. The absorbent article according to claim 1, wherein the absorbent article further comprises an inner coversheet and an outer coversheet.

22. The absorbent article according to claim 21, wherein the absorbent core is not joined to the outer coversheet in any of the lower thickness regions.

23. The absorbent article according to claim 1, wherein the minimum thickness of the article is at least 3 mm.

24. The absorbent article according to claim 1, wherein the minimum thickness of the article is at least 5 mm.

25. The absorbent article according to claim 1, wherein the absorbent article is a sanitary towel, a panty liner, an incontinence pad, or a diaper.

26. The absorbent article according to claim 1, wherein the first and second lower thickness regions are distinct regions, and a region having the average thickness of the absorbent core is disposed transversely between the first and second lower thickness regions.

27. The absorbent article according to claim 2, wherein the first, second and third lower thickness regions are distinct regions, and a region having the average thickness of the absorbent core is disposed transversely between the third lower thickness region and the first and second lower thickness regions.

28. The absorbent article according to claim 4, wherein the fourth and fifth lower thickness regions are distinct regions, and a region having the average thickness of the absorbent core is disposed transversely between the fourth and fifth lower thickness regions.

* * * * *